(12) United States Patent
Cole

(10) Patent No.: US 8,765,698 B2
(45) Date of Patent: Jul. 1, 2014

(54) METHODS AND PRODUCTS FOR REAWAKENING RETROCYCLINS

(75) Inventor: Alexander M. Cole, Chuluota, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 12/699,389

(22) Filed: Feb. 3, 2010

(65) Prior Publication Data

US 2011/0190385 A1 Aug. 4, 2011

(51) Int. Cl.
*A61K 31/70* (2006.01)
*C12N 15/00* (2006.01)

(52) U.S. Cl.
USPC .................................. 514/36; 514/37; 514/41

(58) Field of Classification Search
USPC ................................................ 514/36, 37, 41
See application file for complete search history.

(56) References Cited

U.S. PATENT DOCUMENTS

| | | | | |
|---|---|---|---|---|
| 5,840,702 | A * | 11/1998 | Bedwell .......................... | 514/23 |
| 7,749,971 | B2 * | 7/2010 | Bedwell et al. .................. | 514/35 |
| 2002/0095135 | A1* | 7/2002 | Meeker et al. .................. | 604/522 |
| 2002/0123470 | A1* | 9/2002 | Clark ............................... | 514/36 |
| 2005/0261210 | A1* | 11/2005 | Bhatnagar et al. .............. | 514/35 |
| 2005/0272645 | A1* | 12/2005 | Lehrer et al. ........................ | 514/9 |
| 2008/0207538 | A1* | 8/2008 | Lawrence et al. ................ | 514/41 |
| 2009/0093418 | A1* | 4/2009 | Bassov et al. .................... | 514/25 |

OTHER PUBLICATIONS

Venkataraman et al. Reawakening retrocyclins: Ancestral human defensins active against HIV-1. Plos Biology 7:0720-0729, 2009.*
Cole et al. The retrocyclin analogue RC-101 prevents human immunodefficiency virus type 1 infection of a model human cervicovaginal tissue construct. Immunology 121:140-145, 2007.*
Yasin et al. Theta defensins protect cells from infection by herpes simplex virus by inhibiting viral adhesion and entry. J. Virology 78:5147-5156, 2004.*
Nguyen et al. Evolution of primate theta-defensins: a serpentine path to a sweet tooth. Petptides 24:1647-1654, 2003.*
Bokazhanova, A et al., "The epidemiology of HIV and AIDS in the world", Nov. 2006, Coll Antropol, vol.30, Suppl 2, pp. 3-10.
Titti, F et al., "Problems and emerging approaches in HIV/AIDS vaccine development", 2007, Expert Opin Emerg, Drugs, vol. 12, pp. 23-48.
Munk C et al. "The theta-defensin, retrocyclin, inhibits HIV-1 entry", AIDS Res Hum Retroviruses, vol. 19, pp. 875-881.
Cole AM et al., "Retrocyclins: using past as prologue", 2004, Curr Protein Pept Sci, vol. 5, pp. 373-381.
Owen SM et al., "RC-101, a retrocyclin-1 analogue with enhanced activity against primary HIV type 1 isolates", 2004, AIDS Res Hum Retroviruses, vol. 20, pp. 1157-1165.
Ganz T. "Defensins and host defense", 1999, Science vol. 286, pp. 420-421.
Cole, AM, "Minidefensins and other antimicrobial peptides:candidate anti-HIV microbicides" 2003, Expert Opin Ther Targets, vol. 7, pp. 329-341.
Tang, YQ et al. "A Cyclic Antimicrobial Peptide Produced in Primate Leukocytes by the Ligation of Two Truncated à- Defensins", 1999, Science, vol. 286, pp. 498-502.
Trabi, M. et al., "Three-dimensional structure of RTD-1, a cyclic antimicrobial defensin from Rhesus macaque leukocytes", 2001, Biochemistry, vol. 40, pp. 4211-4221.
Tran, D. et al "Homodimeric theta-defensins from Rhesus macaque leukocytes—Isolation, synthesis, antimicrobial activities, and bacterial binding properties of the cyclic peptides", 2002, Journal of Biological Chemistry, vol. 277, pp. 3079-3084.
Venkataraman, N et al "Cationic polypeptides are required for anti-HIV-1 activity of human vaginal fluid", 2005, J Immunol vol. 175, pp. 7560-7567.
Gallo S A et al., "Theta defensins prevent HIV-1 Env-mediated fusion by binding gp41 and blocking 6-helix bundle formation", 2006, Journal of Biological Chemistry vol. 281, pp. 18787-18792.
Fuhrman, C A et al., "Retrocyclin RC-101 overcomes cationic mutations on the heptad repeat 2 region of HIV-1 gp41", 2007, FEBS J vol. 274, pp. 6477-6487.
Cole, A L et at, "HIV-1 adapts to a retrocyclin with cationic amino acid substitutions that reduce fusion efficiency of gp41", 2006, J Immunol vol. 176, pp. 6900-6905.
Keeling, K M et al., "Clinically relevant aminoglycosides can suppress disease-associated premature stop mutations in the IDUA and P53 cDNAs in a mammalian translation system", 2002, J Mol Med vol. 80, pp. 367-376.
Wilschanski, M et al., "Gentamicin-induced correction of CFTR function in patients with cystic fibrosis and CFTR stop mutations", 2003, N. Engl J Med, vol. 349, pp. 1433-1441.
Lai, C H et al., "Correction of ATM gene function by aminogiycoside-induced read-through of premature termination codons", 2004, Proc Natl Acad Sci USA, vol. 101, pp. 15676-15681.
Brooks, D A, et al. "Stop-codon read-through for patients affected by a lysosomal storage disorder", 2006, Trends Mol Med. vol. 12, pp 367-373.
Nudelman. I et al., "Redesign of aminoglycosides for treatment of human genetic diseases caused by premature stop mutations", 2006, Bioorg Med ChemLett , vol. 16, pp. 6310-6315.
Sermet-Gaudelus, I et al., "In vitro prediction of stop-codon suppression by intravenous gentamicin in patients with cystic fibrosis: a pilot study", 2007, BMC Med 5. 5.
Zingrnan, L V et al., "Aminoglycoside-induced translational readthrough in disease: overcoming nonsense mutations by pharmacogeneuc therapy", 2007, Clin Pharmacol Thee vol. 81, pp. 99-103.
Lynch, S R et al., "Structural origins of aminoglycoside specificity for prokaryotic ribosomes", 2001, J Mol Biol vol. 306, pp. 1037-1058.

(Continued)

*Primary Examiner* — Quang Nguyen
(74) *Attorney, Agent, or Firm* — Timothy H. Van Dyke; Beusse, Wolter, Sanks, Mora & Maire, P.A.

(57) ABSTRACT

Products and methods are provided for the restoring the endogenous expression of theta-defensins, such as retrocyclin-1, in mamallian cells. The present invention also includes products and methods for inhibiting sexually transmitted virus entry, e.g., HIV-1 virus entry, into a mammalian cell via, for example, administering to a subject an amount of a read-through mediating agent sufficient to induce exogenous expression of an amount of retrocyclin nonapeptides in the mammalian cell.

2 Claims, 7 Drawing Sheets

(56) References Cited

OTHER PUBLICATIONS

Lynch, S R et al., "Structure of a eukaryotic decoding region A-site RNA", 2001 J Mol Biol, vol. 306, pp. 1023-1035.

Tanguay, R L et al., "Translational efficiency is regulated by the length of the 3' untranslated region", 1996, Mol Cell Biol vol. 16, pp. 146-156.

Daly, N L et al., "Retrocyclin-2: structural analysis of a potent anti-HIV theta-defensin", 2007, Biochemistry, vol. 46, pp. 9920-9928.

Mazumder, B et al., "Translational control by the 3'-UTR: the ends specify the means", 2003, Trends Biochem Sci, vol. 28, pp. 91-98.

Du, M et al., "PTC124 is an orally bioavailable compound that promotes suppression of the human CFTR-G542X nonsense allele in a CF mouse model", 2008, Proc Natl Acad Sci USA vol. 105, pp. 2064-2069.

Welch. E M et al., "PTC124 targets genetic disorder caused by nonsense mutations" 2007, Nature, vol. 447, pp. 87-91.

Gallagher, R et al., "Characterization of the continuous, differentiating myeloid cell line (HL-60) from a patient with acute promyelocytic leukemia", 1979, Blood, vol. 54, pp. 713-733.

Collins, S J et al., "Continuous growth and differentiation of human myeloid leukaemic cells in suspension culture", 1997, Nature, vol. 270, pp. 347-349.

Platt, E J et al. "Effects of CCR5 and CD4 cell surface concentrations on infections by macrophagetropc isolates of human immunodeficiency virus type 1", 1998, J Virol, vol. 72, pp. 2855-2864.

Deng, H et al., "Identification of a major co-receptor for primary isolates of HIV-1", 1996, Nature, vol. 381, pp. 661-666.

Landau, N. R et al., "Packaging system for rapid production of murine leukemia vials vectors with variabie tropism", 1992, J Virol, vol. 66, pp. 5110-5113.

Lusso, P et al, "Growth of macrophage-tropic and primary human immunodeficiency virus type 1 (HIV-1) isolates in a unique CD4+ T-cell clone (PM1): failure to downregulate CD4 and to interfere with cell-line-tropic HIV-1" 1995, J Virol vol. 69, pp. 3712-3720.

Cole, Alexander M. et al., "Retrooyolin: A primate peptide that protects cells from infection by T-and M-tropic strains of HIV-1", PNAS, Feb. 2002, vol. 99, No. 4, pp. 1813-1818.

Zarocostas, John, "WHO and UN slash their estimates of global HIV prevalence", Nov. 2007 BMJ, vol. 335 (7629), pp. 1069.

Wang, Wei et al., "Activity of α- and ⊖- Defensins against Primary Isolates of HIV-1", 2004; Journal of Immunology, vol. 173, pp. 515-520.

* cited by examiner

METHODS AND PRODUCTS FOR REAWAKENING RETROCYCLINS

FIELD OF THE INVENTION

The present invention relates to products and methods for the restoring the endogenous expression of theta-defensins, such as retrocyclin polypeptides, in a host cell. The present invention also relates to products and methods for inhibiting HIV-1 virus entry into a host cell via, for example, administering to a subject an amount of a read-through mediating agent sufficient to induce exogenous expression of an amount of retrocyclin polypeptides in the host cell.

BACKGROUND OF THE INVENTION

Nearly 33 million people are infected with HIV worldwide [1,2], and despite extensive efforts, there are no effective vaccines or other countermeasures to protect against HIV transmission [3]. Previous attempts to find effective anti-HIV agents have determined that certain synthetic θ-defensins called "retrocyclins" or "retrocyclin polypeptides" are potent inhibitors of HIV-1 infection [4-8]. Retrocyclins belong to a large family of antimicrobial peptides known as defensins, all of which are cationic, tri-disulfide bonded peptides that have important roles in innate host defense. Based on the position of the cysteines and the disulfide bonding pattern, defensins are grouped into 3 subfamilies: α-defensins, β-defensins and θ-defensins [9, 10].

θ-Defensins such as retrocyclin have a cyclic peptide backbone, derived from the head-to-tail-ligation of two nonapeptides that each contributes nine amino acids to form the 18 residue mature polypeptide [11]. θ-Defensins are the only known cyclic peptides in mammals and were originally isolated from rhesus macaque leukocytes and bone marrow [11-13]. While θ-defensin peptides, e.g., retrocyclin polypeptides, are produced in old world monkeys and orangutans, in humans they exist only as expressed pseudogenes [14]. Critically, a premature termination codon in the signal peptide portion of human retrocyclin mRNA prevents its translation. The retrocyclin gene is otherwise remarkably intact, showing 89.4% identity with rhesus θ-defensins. Its genetic information was utilized to recreate retrocyclins synthetically and confirm their activity against both X4 and R5 strains of HIV-1 [4-7]. To date, however, there has not yet been developed an agent or process for restoring the mammalian body's ability to endogenously produce retrocyclin peptides.

DETAILED DESCRIPTION OF THE INVENTION

Figure 1:
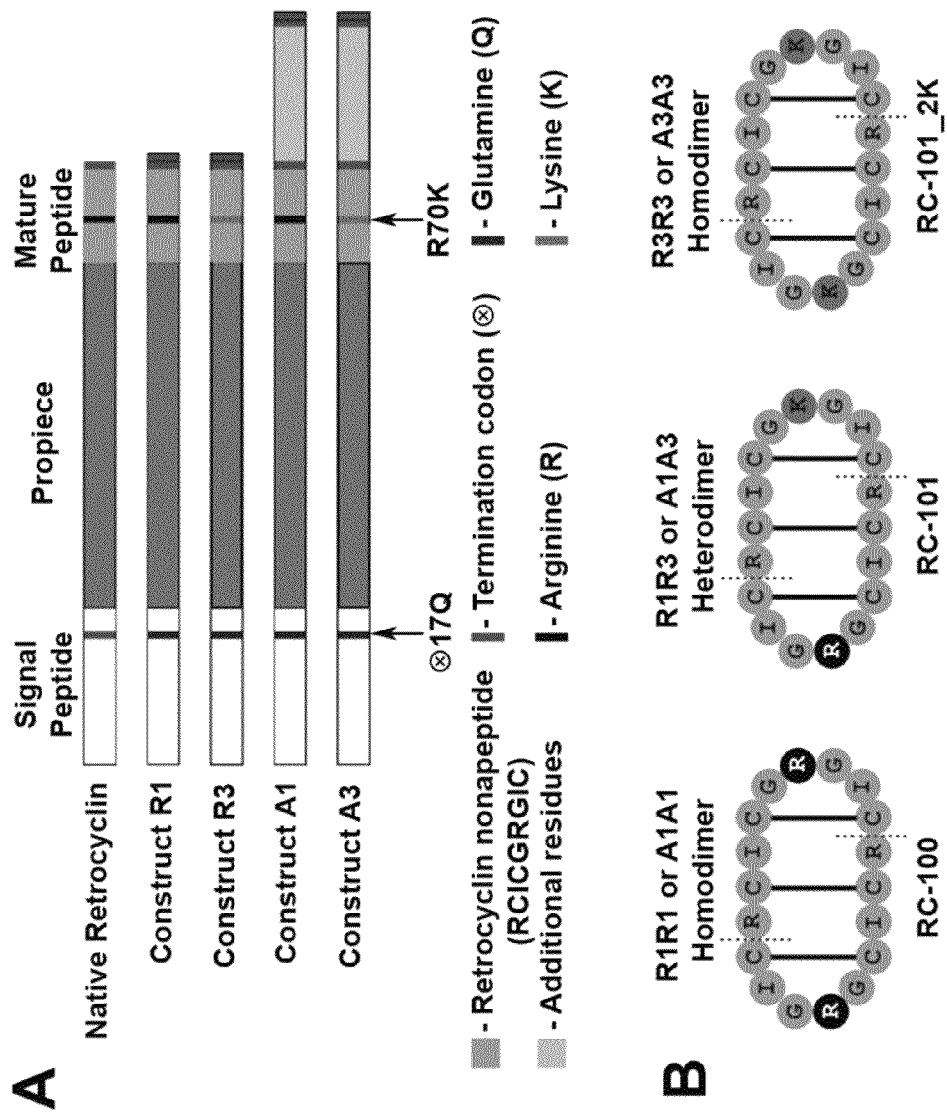
FIG. 1: Design of retrocyclin constructs. (A) Shows a schematic of the 4 constructs (R1, R3, A1 and A3) used for stable transfections along with native retrocyclin cDNA, which encodes the retrocyclin nonapeptide (SEQ ID NO. 10). All constructs have two termination codons at the end to ensure read-fidelity. Constructs A1 and A3 contain additional downstream residues while constructs R1 and R3 lack them. The two arrows indicate the position at which the two site-directed mutagenesis (⊗ 17Q and R70K) were performed. (B) Shows the three possible mature retrocyclin peptides that could be formed from the constructs, homodimers of R1 or A1 encoding RC-100 (wild type retrocyclin), heterodimers of A1 and A3 or R1 and R3 encoding RC-101 (single lysine congener) and homodimers of R3 or A3 encoding RC-101_2K (double lysine congener).

The present inventor has surprisingly restored the endogenous expression of the evolutionarily lost retrocyclin polypeptides in host cells by multiple processes. In one embodiment, the ability to endogenously produce retrocyclin polypeptides is done by ablating an existing premature termination codon using site-directed mutagenesis and introducing the modified sequence into a host cell via a delivery and expression vector (or "delivery vector"). In another embodiment, the ability to endogenously produce retrocylin peptides is done via administering an amount of a read-through mediating agent that is effective to read-through an existing premature codon to allow for expression of the retrocyclin polypeptide. In this way, utilizing aspects of the present invention, mammalian host cells may synthesize biologically active retrocyclin polypeptides for the first time. The produced biologically active retrocyclin polypeptides may be utilized as an effective and natural way of combating sexually transmitted infections (STI's), e.g., HIV-1 infection. For example, in an aspect of the present invention, there is provided a method of inhibiting sexually transmitted virus entry into a human cell of a mammalian subject comprising administering an amount of a read-through mediating agent, e.g., aminoglycosides effective to produce retrocyclin polypeptides in the mamallian subject.

In accordance with one aspect of the present invention, there is provided a process for inducing expression of a retrocyclin polypeptide in a host cell. The process comprises introducing a delivery vector into the host cell, wherein the delivery vector comprises a polynucleotide having a nucleotide sequence that encodes for a retrocyclin polypeptide comprising a sequence according to SEQ. ID. NO: 8 or SEQ. ID. NO: 9, or variants thereof. The introduction of the delivery vector into the host cell results in the expression of the retrocyclin polypeptide in the host cell.

In accordance with another aspect of the present invention, there is provided a delivery and expression vector for transfecting a cell with an expression construct that encodes for a retrocyclin polypeptide. The expression construct comprises a polynucleotide sequence encoding SEQ. ID. NO: 8 or SEQ. ID. NO: 9, or variants thereof. The expression construct comprises SEQ. ID. NO: 1, SEQ. ID NO: 2, SEQ. ID. NO: 3, or SEQ. ID NO: 4, or variants thereof.

In accordance with another aspect of the present invention, there is provided a method for reducing virus entry into a host cell of a mammalian subject comprising administering to the mammalian subject an amount of an expression construct encoding a retrocyclin polypeptide. The expression construct comprises a polynucleotide sequence encoding SEQ. ID. NO: 8 or SEQ. ID. NO: 9, or variants thereof.

The terms "variant or variants" as used herein refer to nucleotide and polypeptide sequences wherein the nucleotide or amino acid sequence exhibits substantial identity with the nucleotide or amino acid sequence of the SEQ ID NOs, set forth herein, preferably 75% sequence identity and most preferably 90-95% sequence identity to the sequences of the present invention: provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The terms "variant" or "variants" also include homologous sequences which hybridize to the sequences of the invention under standard or preferably stringent hybridization conditions familiar to those skilled in the art. Examples of the in situ hybridization procedure typically used are described in (Tisdall et al., 1999); (Juengel et al., 2000). Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art. In addition, "variant" or "variants" may encompass amino acid sequences comprising one amino acid substitution with SEQ. ID. NO: 8 or SEQ. ID. NO: 9 (as set forth herein) or two consecutive amino acid substitutions with SEQ. ID. NO: 8 or SEQ. ID. NO: 9.

In one embodiment, the variants of SEQ. ID. NO: 8 or SEQ. ID. NO: 9 as set forth herein comprise a polypeptide having the following sequence:

```
(I)   Cys   (II)   Cys   (III)   (IV)   (V)   (VI)   Cys
wherein (I) = Arg or Lys
wherein (II) = Ile, Leu, Glu, or Val
wherein (III) = Gly, Ile, Leu, or Val
wherein (IV) = Arg or Lys
wherein (V) = Gly, Ile, Leu, or Val
wherein (VI) = Ile, Leu, Glu, or Val.
```

The delivery vector may be a viral or non-vector as is known in the art, including but not limited to, single-stranded and double-stranded nucleic acid vectors as well as DNA, RNA, and DNA/RNA chimeric vectors. Exemplary viral vectors include, but are not limited to, adenovirus, herpesvirus, lentivirus, parvovirus (e.g., AAV), baculovirus and Epstein Barr Virus vectors. Exemplary non-viral vectors include, but are not limited to, plasmid, phage, yeast artificial chromosomes (YACs), Bacterial Artificial Chromosomes (BACs), and naked DNA vectors (e.g., by liposomal delivery), or synthetic nucleotide vectors (e.g., vectors that are generated by PCR methods or oligonucleotide synthesis, as are known in the art). In one particular embodiment, the delivery vector is an adeno-associated virus (AAV) vector, e.g., in the form of AAV viral particles. In another embodiment, the delivery vector is a plasmid. Plasmids are "naked" DNA and do not encode genes necessary to encase the genetic material for transfer to a new host. The delivery vectors described herein may be used in both in vitro and in vivo studies.

In one embodiment, the host cell is a mammalian host cell, e.g., a human host cell. By way of example only, the host cell may be an epithelial cell or a myeloid cell, including cells from the spleen, bone marrow, thymus, testis, skeletal muscle, nasal, nasal mucosa, and cervicovaginal epithelia.

The expression system comprises multiple polynucleotides having a nucleotide sequence that when expressed will produce a retrocyclin polypeptide as will be explained below. In one embodiment, the encoded retrocyclin polypeptide is a homodimer comprising a sequence according to SEQ. ID. NO: 8, or variants thereof. In a particular embodiment, the retrocyclin polypeptide comprises a homodimer comprising two nonapeptides according to SEQ. ID. NO: 8, or variants thereof. The nucleotide sequence, which encodes the retrocyclin polypeptide according to SEQ. ID. NO: 8, or variants thereof, may be represented by SEQ. ID. NO: 1 or SEQ. ID NO: 2.

In another embodiment, the encoded retrocyclin polypeptide is a homodimer comprising a sequence according to SEQ. ID. NO: 9, or variants thereof. In a particular embodiment, the retrocyclin polypeptide comprises a homodimer comprising two nonapeptides according to SEQ. ID. NO: 9, or variants thereof. The nucleotide sequence, which encodes the retrocyclin polypeptide according to SEQ. ID. NO: 9, or variants thereof, may be represented by SEQ. ID. NO: 3 or SEQ. ID NO: 4.

In yet another embodiment, the encoded retrocyclin polypeptide forms a heterodimer comprising a nonapeptide having a sequence according to SEQ. ID. NO: 8, or variants thereof, and a nonapeptide having a sequence according to SEQ. ID. NO: 9, or variants thereof. The nucleotide sequence, which encodes the retrocyclin nonapeptide according to SEQ. ID. NO: 8, or variants thereof, may be represented by SEQ. ID. NO: 1 or SEQ. ID NO: 2. The nucleotide sequence, which encodes the retrocyclin nonapeptide according to SEQ. ID. NO: 9, or variants thereof, may be represented by SEQ. ID. NO: 3 or SEQ. ID NO: 4.

Turning now to the figures, FIG. 1A shows four modified retrocyclin-expressing constructs (labeled R1, R3, A1 and A3 for convenience). Critically, the expression constructs each correct a premature termination codon found in the naturally occurring form of the retrocylin peptide mRNA to enable expression of the retrocyclin polypeptide. As shown, the termination codon at ($\otimes$17Q) is replaced with a suitable codon, such as one encoding for glutamine. Aside from the corrected premature termination codon ($\otimes$17Q), all of these constructs (R1, R3, A1, A3) were engineered to contain two termination codons at the end of the gene to ensure read-fidelity. Constructs with an "R" designation terminate after the retrocyclin portion of the gene, while constructs with an "A" designation contain the retrocyclin portion with additional downstream residues that might be critical for translation and/or processing [14, 28].

Figure 7:
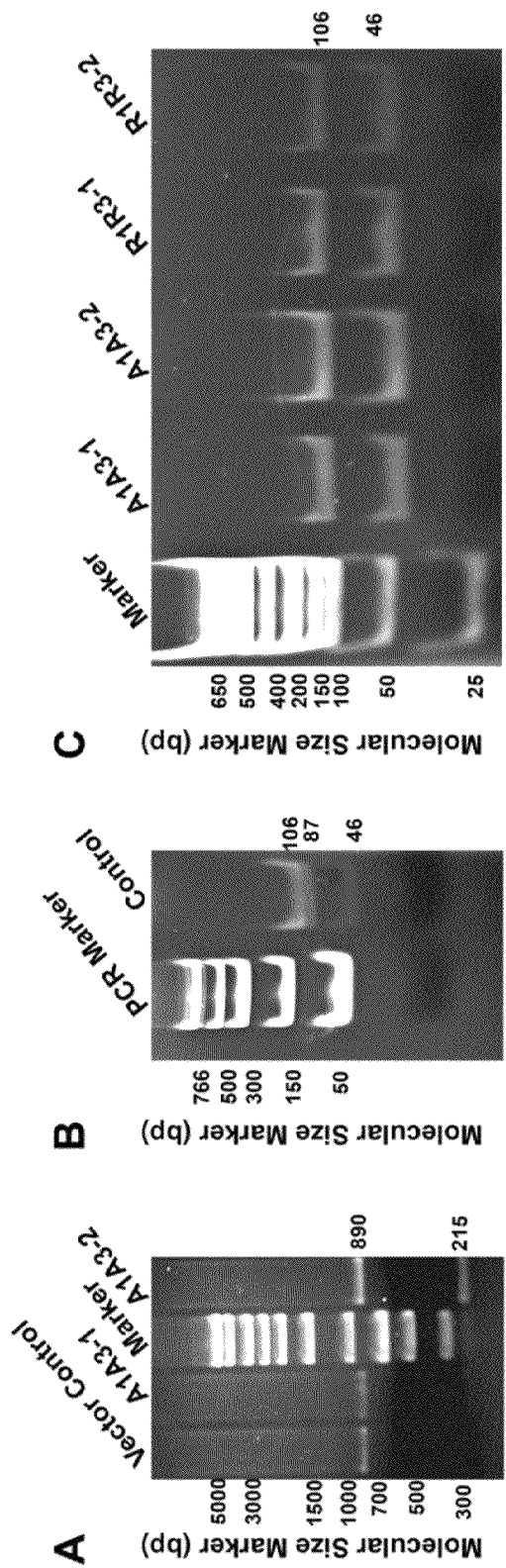
FIG. 7: Verification of stable transfection of retrocyclin constructs. Analysis of the genomic DNA and RNA of transfected HL60 cells confirms the stable transfection and transcription of rescued retrocyclin constructs respectively. (A) PCR on genomic DNA template from transfected HL60 cells shows a 215 bp fragment representing retrocyclin cDNA construct and a 890 bp fragment of native retrocyclin gene in the genomic DNA of A1A3 clones but not in the Vector control (VC) cells. (B, C) Correction of the premature termination codon of retrocyclin cDNA introduces an additional HpyCH4V restriction site the middle of a 87 bp cDNA fragment. RNA isolated from HL60 cells (control, R1R3 clones 1 & 2 and A1A3 clones 1 & 2) was used to make cDNA. Retrocyclin constructs were amplified by PCR using the cDNA as template and digested using HpyCH4V restriction enzyme. Electrophoresis of the digested PCR products shows the expected 87 bp fragment in control cells (B) and the expected absence of 87 bp fragment in R1R3 and A1A3 clones (C). All the products were also verified by DNA sequencing.

Constructs with a "1" designation (A1, R1) do not have any additional residues mutated, while constructs with a "3" designation (A3, R3) have the additional Arg→Lys mutation (R70K) encoding a RC-101 polypeptide. HL60 cells (a human promyelocytic cell line) were co-transfected by electroporation with either R1 and R3, or A1 and A3, and propagated in the presence of G418 (300 μg/ml) to create stably transfected cell lines. In another embodiment, host cells may be transfected with any one of R1, R3, A1, and A3 individually. Stable transfection was verified by analyzing genomic DNA and mRNA primers (FIG. 7). Since two different constructs (R1, R2 and A1, A3) were co-transfected for each condition, combinatorially it would be possible to generate three different retrocyclin peptides as illustrated in FIG. 1B. For example, if cells were co-transfected with the R1 and R3 constructs, they could theoretically generate a heterodimer (R1R3) or homodimers (R1R1 or R3R3). Similarly, if cells were co-transfected with the A1 and A3 constructs, they could theoretically generate a heterodimer (A1A3) or homodimers (A1A1 or A3A3). FIG. 1B specifically shows three possible mature retrocyclin polypeptides that could be formed from the constructs: homodimers of R1 or A1 encoding RC-100 (wild type retrocyclin), heterodimers of A1 and A3 or R1 and R3 encoding RC-101 (single lysine congener) and homodimers of R3 or A3 encoding RC-101_2K (double lysine congener).

Figure 2:
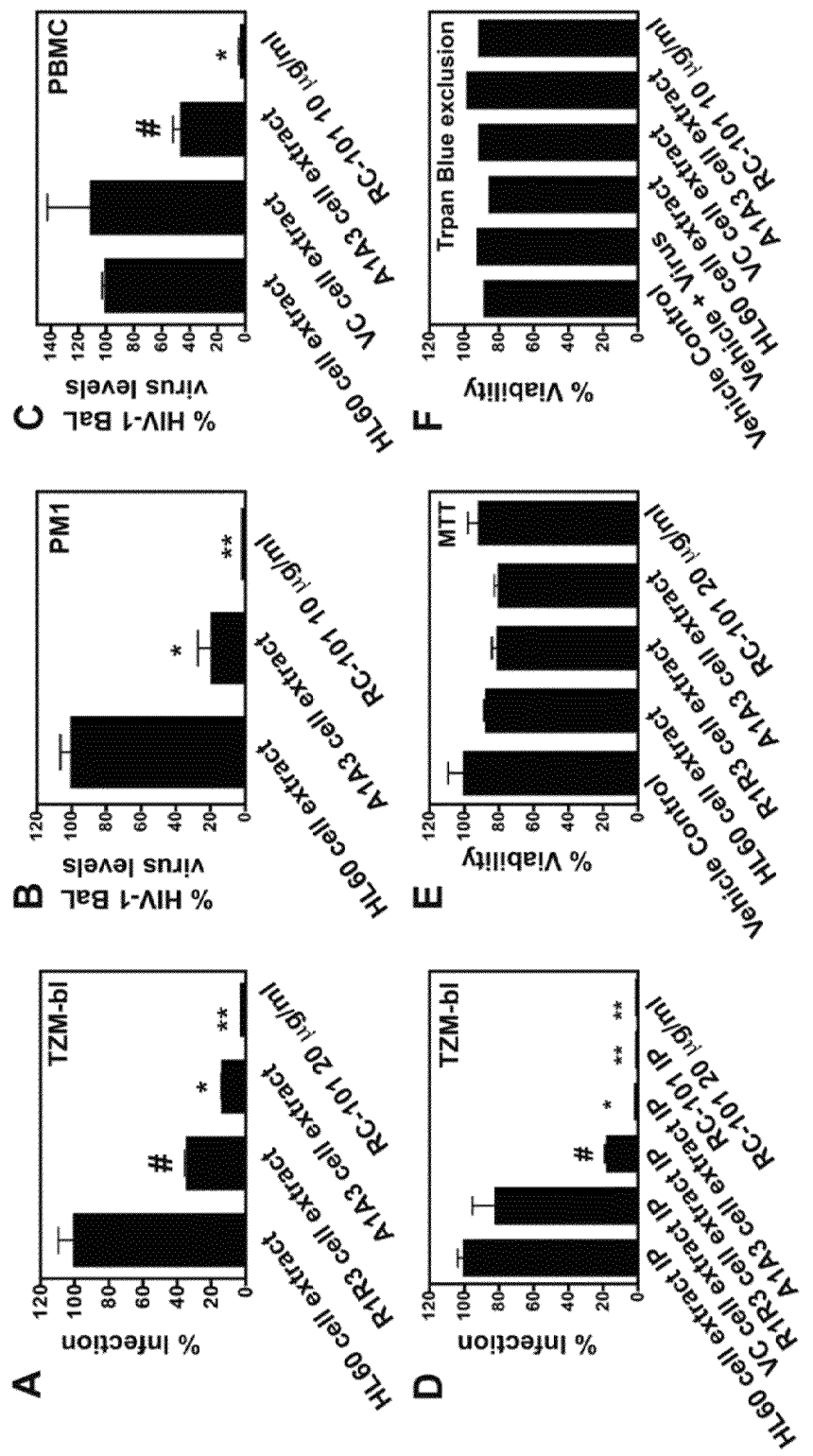
FIG. 2: Extracts from HL60 cells stably transfected with retrocyclin constructs are active against HIV-1 infection. (A) TZM-bl cells were treated with extracts or peptide as indicated in the figure and infected with HIV-1 BaL (6.5 ng/ml p24) for 24 hr. Infection was measured as percent luciferase activity compared to cells treated with control cell extract (Average RLU of control HL60 extract=178,200). (B, C) PM1 cells and PBMCs were treated with extracts or peptide as indicated and infected with HIV-1 BaL (2 ng/ml p24) and cultured for 5-9 days. Bars represent percent BaL HIV-1 levels in the supernatants collected on days 5 (B) and 9 (C). The amount of p24 in PM1 cells treated with control extract=76.85 ng/ml and in PBMCs treated with control extracts=55.99 ng/ml. (D) TZM-bl cells were treated with immunopurified (IP) extracts or peptides as indicated and infected with BaL HIV-1 (p24=2 ng/ml) for 24 hr. Infection was quantified as percent luciferase activity compared to cells treated with control HL60 cell IP extracts (Average RLU=764,460). Error bars represent SEM. n=3-4, #P<0.004, *P<0.002, **P<0.0005. (E) Cellular viability of TZM-bl cells treated with HL60 acid extracts as indicated was determined by measuring the reduction of MTT after 24 h (n=3). Bars represent percent viability as compared to vehicle control and error bars represent SEM. (F) Cell death was monitored in PBMCs treated with the acid extracts by a trypan blue exclusion assay on day 9 (n=1).

As shown in FIGS. 2A-2F, the correction of the termination codon in the retrocyclin constructs restored the translation of biologically active retrocyclin polypeptides. The infection of TZM-bl cells with HIV-1 BaL was significantly reduced when the cells were treated with cellular acid extracts of R1R3 cells (P<0.004) and A1A3 cells (P<0.002) (FIG. 2A). A standard tetrazolium MTT assay revealed that the extracts did not affect cellular metabolism at the concentrations used in the experiment (FIG. 2E). Addition of A1A3 cell extracts to HIV-1 infected PM1 cells (FIG. 2B) and PBMCs (FIG. 2C) showed a significant (P<0.002 and P<0.004 respectively) decrease in the viral titer as compared to cells treated with control HL60 cell extract. A trypan blue exclusion assay was performed in PBMCs to monitor cell viability (FIG. 2F). Next, R1R3 and A1A3 cell extracts were affinity purified using anti-RC-101 antibody and confirmed the antiviral activity in a luciferase-based assay system (FIG. 2D). Interestingly, A1A3 cell extracts were found to be consistently more active than equivalent amounts of R1R3 cell extract, which may suggest a role for the downstream residues in retrocyclin processing. These results indicated that biologically active recombinant retrocyclin peptides can be synthesized in human promyelocytic cells.

Figure 3:
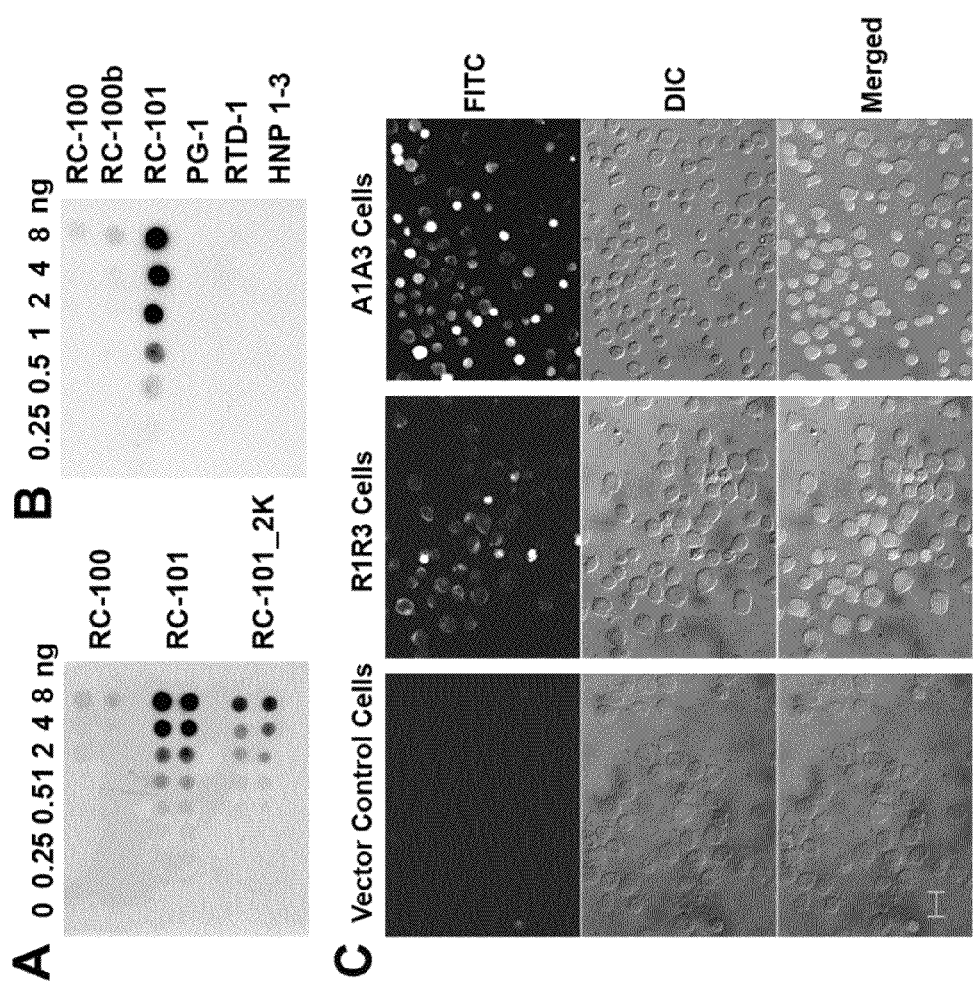
FIG. 3: Immunofluorescence staining of stably transfected HL60 cells reveals retrocyclin peptides. (A) Retrocyclin peptides RC-100, RC-101 and RC-101_2K peptides (in duplicates) and (B) RC-100, RC-100b, RC-101, protegrin-1 (PG-1), rhesus theta defensin-1 (RTD-1), and human neutrophil peptides 1-3 (HNP 1-3) were dotted (0-8 ng/4 μl dot) on a PVDF membrane and subjected to immuno-dotblot analysis. (C) Vector control, R1R3 and A1A3 (100,000 cells each) were fixed onto glass slides and incubated with rabbit anti-RC-101 antibody followed by biotinylated goat anti-rabbit IgG secondary antibody and then stained using FITC-avidin. Slides were visualized using Zeiss Axiovert 200M microscope system at 40× magnification. The three rows show FITC staining, DIC and the merged image respectively. Scale bar represents 20 μm.

The presence of the resulting expressed retrocyclin peptides in promyelocytic cells were confirmed using immunostaining, particularly by the immunofluorescence staining of stably transfected HL60 cells. As shown in FIGS. 3A and 3B, for example, immuno-dotblot analyses revealed that an anti-RC-101 antibody specifically recognized lysine-containing human retrocyclin analogs (synthetic RC-101 and RC-101_2K) and RC-100 (i.e. wild type form) to a lesser extent (FIG. 3A), but not human neutrophil peptides 1-3, or peptides with very similar tertiary structure including rhesus theta defensin-1 (RTD-1) and protegrin-1 (PG-1) (FIG. 3B). As shown in FIG. 3C, an anti-RC-101 antibody was used to visualize the expressed retrocyclin polypeptides in the stably transfected HL60 cells by immunofluorescence staining, which revealed that cells expressing R1R3 heterodimer retrocyclin polypeptides and cells expressing A1A3 retrocyclin polypeptides were brightly stained as compared to Vector Control (VC) cells. Slides treated with pre-immune serum showed no staining (data not shown). The staining of cells producing A1A3 retrocyclin polypeptides was brighter than cells expressing R1R3 retrocyclin polypeptides and the morphology of A1A3 was smaller than VC cells.

Figure 4:
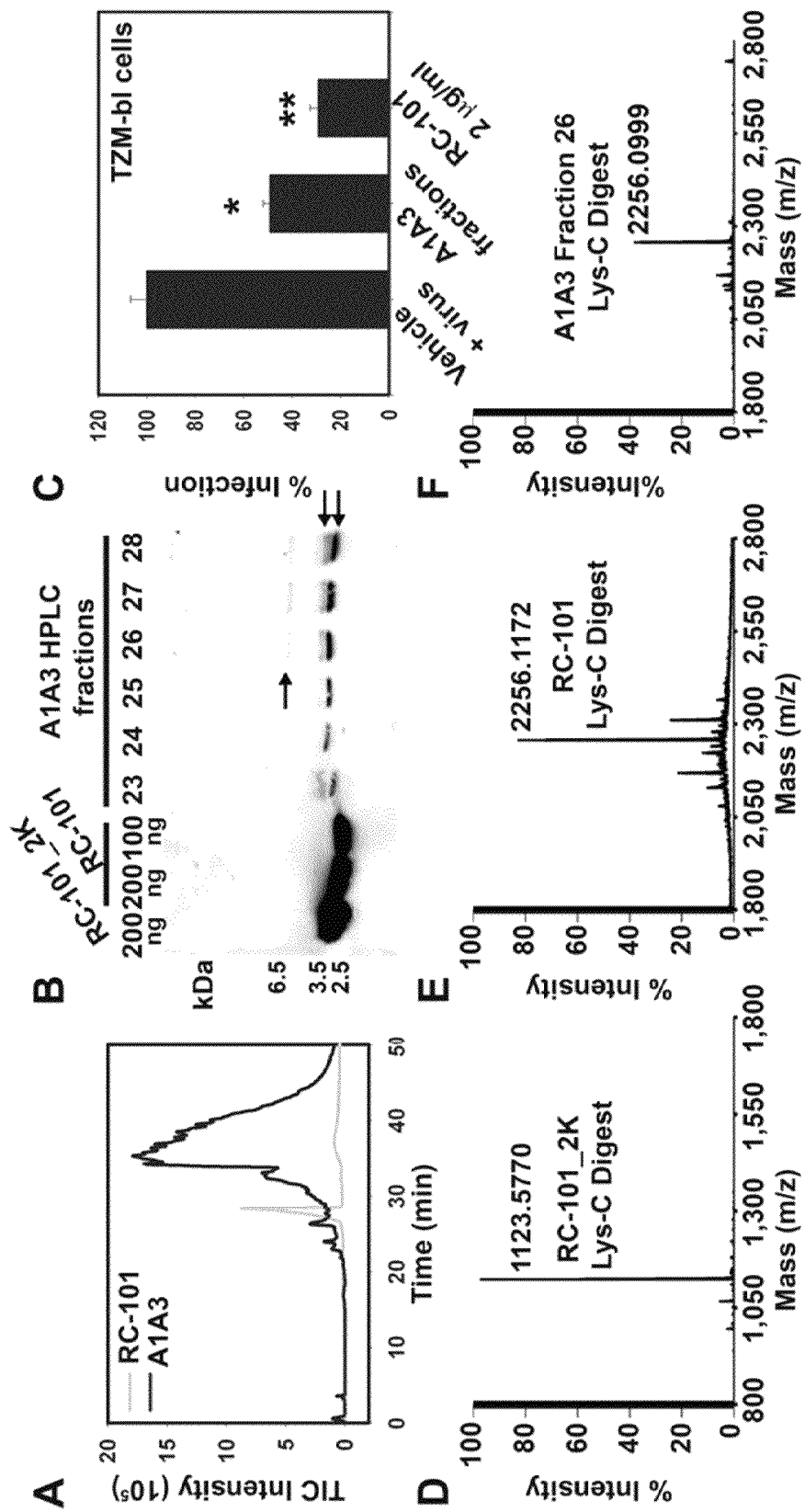
FIG. 4: Stably transfected promyelocytic cells produce retrocyclin. (A) Shows the RP-HPLC trace of A1A3 cell extract (from $10^8$ cells) and 50 μg of synthetic RC-101. (B) Western blot of A1A3 HPLC fractions (23-28 min) using rabbit anti-RC-101 antibody. The arrows indicate the multimeric forms of retrocyclin observed in A1A3 fractions. (C) TZM-bl cells were infected with HIV-1 (p24=2 ng/ml) in the presence or absence of pooled A1A3 fractions (final dilution 1:6 in D10) or 2 μg/ml of RC-101 for 24 hr. Infection was quantified by luciferase measurement (Average RLU of Vehicle control with virus=85,450). Error bar represents SEM and n=3-6, *P<0.0015 **P<0.0001. MALDI-TOF MS spectra of Lys-C digested (D) synthetic RC-101_2K, (E) synthetic RC-101 and (F) A1A3 HPLC fraction 26 reveal that A1A3 cells produce RC-101.

Thereafter, the presence of the expressed retrocyclin peptides from the cell extracts was confirmed. In particular, reverse-phase high pressure liquid chromatography HPLC (RP-HPLC) was utilized to purify the recombinant retrocyclin peptides from stably transfected HL60 cell extracts. FIG. 4A shows the RP-HPLC trace of the A1A3 heterodimer (RC-101) and synthetic RC-101. Synthetic RC-101 was recovered in fractions collected at 26-28 min. A1A3 HPLC fractions collected from 23-30 minutes were analyzed on a 16% Tricine-SDS-gel. Control samples did not contain any protein bands at the expected size while fractions from R1R3 cell extracts revealed protein bands of about 6 kDa size (not shown). A1A3 HPLC fractions revealed multiple protein bands, which were analyzed by western blot (FIG. 4B). The western blot analysis revealed bands at sizes corresponding to a monomer, dimer and trimer of retrocyclin. The presence of multimeric forms of retrocyclin had previously been uncovered by Daly and colleagues [29].

Furthermore, the RP-HPLC purified A1A3 fractions inhibited entry of HIV-1 BaL in TZM-bl cells (FIG. 4C). The $IC_{50}$ of retrocyclin peptides expressed by A1A3 cells (2 µg/ml) was similar to that of synthetic RC-101 (1.25 µg/ml) [8]. It is specifically believed that retrocyclins inhibit the fusion of HIV-1 Env by selectively binding to the C-terminal heptad repeat region on gp41 blocking 6-helix bundle formation [15, 16]. RC-101 is a congener of retrocyclin with a single arginine to lysine substitution that retains structural and functional similarity to retrocyclin [4]. RC-101 exhibited enhanced anti-HIV-1 activity against over two dozen primary isolates from several clades [7, 8], and did not induce inflammation or toxicity in organotypic models of human cervicovaginal tissue [17].

To determine the identity of the retrocyclin peptide expressed by A1A3-expressing cells (cells transfected with the A1 and A3 sequence and expressing an A1A3 heterodimer), an HPLC fraction 26 (collected at 26 minutes) was analyzed by mass spectrometric analysis (MALDI-TOF-MS). Analysis of the A1A3 fraction revealed peaks with masses 1889.775 Da (oxidized) and 1895.890 Da (reduced), which is nearly identical to the expected mass of synthetic cyclic RC-101 (1889.85 Da and 1895.96 Da respectively; data not shown) and is in agreement with reduction of the three disulfide bridges in the molecule. Furthermore, treatment with iodoacetamide yielded mass species of 2238.081 Da for the A1A3 fraction 26 and 2238.071 Da for RC-101 corresponding to the predicted 6-fold-alkylated form of RC-101 (expected mass=2238.097 Da). Comparison of spectrum of the Lys-C digest of reduced/alkylated synthetic RC-101_2K (peak at 1123.577 Da; peptide cleaved at two Lys-Gly bonds; See FIG. 4D), synthetic RC-101 (peak at 2256.097 Da; peptide cleaved at a single Lys-Gly bond; N-terminal sequence determined as: Gly-Ile-Cys-Arg-; See FIG. 4E) and A1A3 fraction 26 (peak at 2256.010 Da) suggests that the A1A3 cells are expressing RC-101 (See FIG. 4F). These data confirmed that correctly folded mature retrocyclin polypeptides can be expressed by human cells.

In accordance with another aspect of the present invention, the inventor has surprisingly found yet another process for expressing retrocyclin nonapeptides endogenously. In particular, the present inventor has found that the use of specific read-through mediating agents enable varying degrees of termination codon read-through to produce retrocyclin nonapeptides. Thus, in one embodiment of the present invention, there is provided a method for inducing the expression of a retrocyclin polypeptide in a mammalian host cell having a naturally-occurring sequence encoding for the retrocyclin polypeptide, wherein the naturally-occurring sequence has a premature termination codon. The process comprises inducing expression of the retrocyclin polypeptide in the mammalian host cell via contacting the mammalian host cell with an amount of a read-through mediating agent effective to read-through the premature termination codon and allow for expression of the retrocyclin nonapeptide. By "an amount of a read-through mediating agent effective to" as used herein, it is meant an amount effective, at dosages and for periods of time necessary to achieve the desired result.

In one embodiment, the read-through mediating agent comprises an aminoglycoside. Thus, the aminoglycoside may include but is not limited to one or more of amikacin, arbekacin, gentamycin, kanamycin, neomycin, netilmicin, paromomycin, rhodostreptomycin, streptomycin, tobramycin, and apramycin. In a particular embodiment, the aminoglycoside is one or more of gentamycin, amikacin, or tobramycin. In another embodiment, the read-through mediating agent is Ataluren (PTC124®) available from PTC Therapeutics, Inc., Plainfield, N.J.

Figure 5:
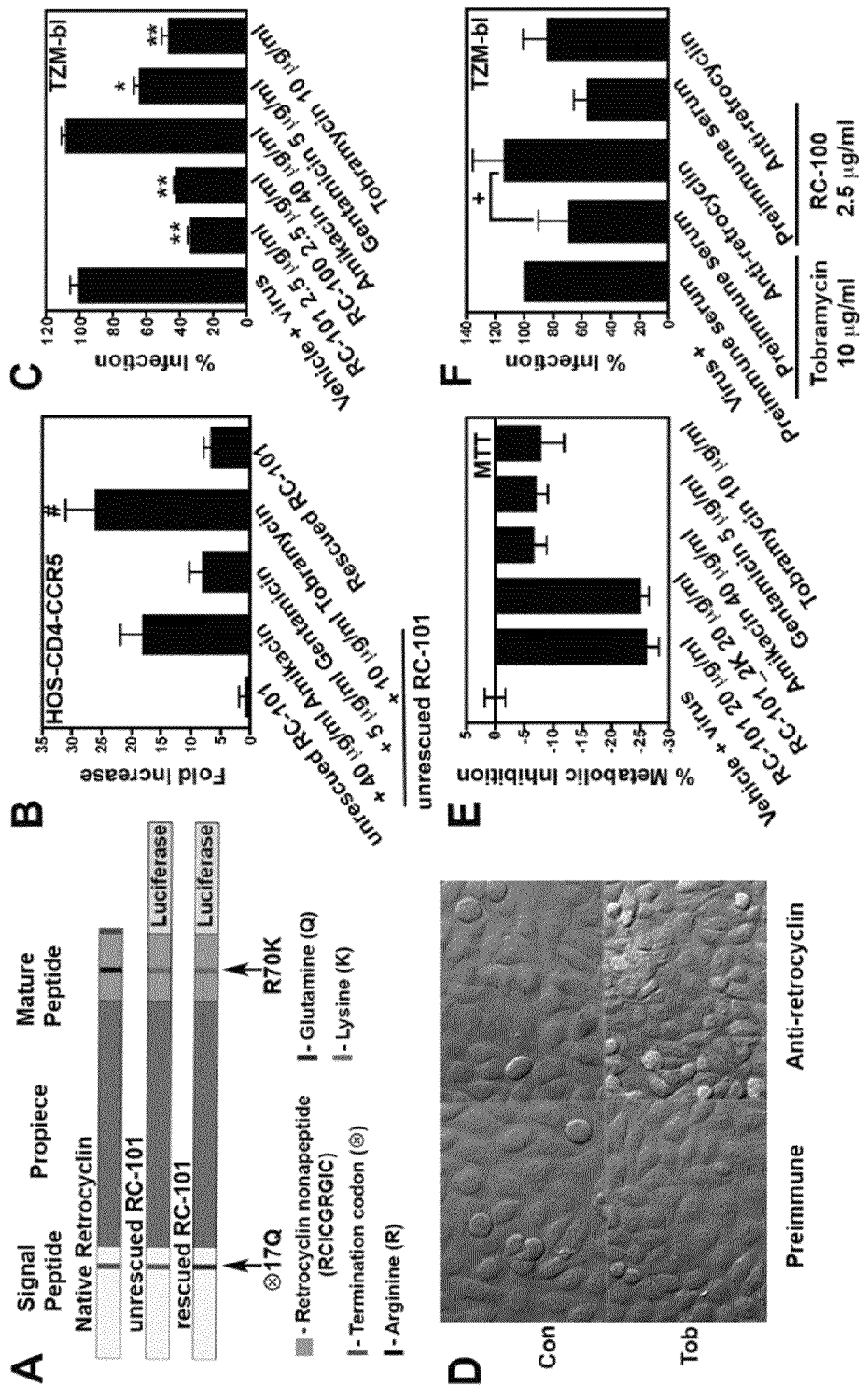
FIG. 5: Aminoglycosides mediate read-through of the premature termination codon within the retrocyclin gene and promote anti-HIV-1 activity. (A) Shows a schematic representation of the luciferase fusion constructs unrescued RC-101 and rescued RC-101 along with native retrocyclin cDNA which encodes the retrocyclin nonapeptide (SEQ ID NO. 10). (B) HOS-CD4-CCR5 cells cultured in antibiotic free medium (D10⁻) were transfected with unrescued RC-101 (negative control) or rescued RC-101 (positive control) plasmids along with phRL-CMV vector (transfection control). The next day transfected cells were treated with PBS for control cells or aminoglycosides at the indicated concentrations and allowed to grow for 24 hr. Read-through was determined by measuring luciferase levels. Data is expressed as fold increase in luciferase expression normalized to renilla levels. (C) TZM-bl cells grown in D10⁻ were treated for 30 min with PBS, RC-101 (2.5 μg/ml), RC-100 (2.5 μg/ml) or aminoglycosides as shown in the figure and infected with HIV-1 BaL (2 ng/ml p24) for 24 hr followed by luciferase measurement. Error bars represent SEM. n=3-6, #$P<0.007$ *$P<0.0005$ **$P<0.0001$. (D) TZM-bl cells cultured on cover slips were treated with PBS (Con) or 10 μg/ml tobramycin (Tob) and then immunostained with rabbit pre-immune or anti-retrocyclin serum using a biotinylated secondary antibody FITC-avidin system. (E) Cellular cytotoxicity was assessed by performing an MTT assay on TZM-bl cells treated with indicated amount of peptide or aminoglycosides (n=3). Bars represent percent metabolic inhibition as compared to control (vehicle+virus). (F) TZM-bl cells, treated with either PBS, tobramycin (10 μg/ml) or RC-100 (2.5 μg/ml), were incubated with preimmune serum or anti-retrocyclin serum as indicated and infected with HIV-1 (p24 of 5 ng/ml). Data is represented as percent infection. Error bars represent SEM. n=3, +$P<0.018$ Statistical significance was determined by two-tailed Student t-test.

Turning again to the figures, the ability of three exemplary aminoglycosides (gentamicin, amikacin, and tobramycin) were tested to induce termination codon read-through of retrocyclin cDNA. The native retrocyclin gene was fused with a luciferase reporter at the C-terminus to create 2 constructs: unrescued RC-101 and rescued RC-101 (positive control) as shown in FIG. 5A. These constructs were transfected into HOS-CD4-CCR5 cells, grown in the presence of varying concentrations of aminoglycosides, and the degree of read-through quantified by measuring luciferase. Application of tobramycin (10 µg/ml) was the most effective, producing a 26-fold increase in read-through ($P<0.0007$; FIG. 5B).

Having thus established the optimal aminoglycoside concentration required to achieve read-through of retrocylin cDNA, it was next determined if aminoglycosides could restore the translation and anti-HIV-1 activity of native retrocyclin peptides. HeLa-derived cells lines, such as TZM-bl cells can natively express retrocyclin mRNA (data not shown). Aminoglycosides were applied to TZM-bl cells and challenged them with HIV-1 BaL. It was found that cells treated with gentamicin and tobramycin significantly ($P<0.0005$ and $P<0.0001$ respectively) inhibited HIV-1 infection as compared to untreated cells (FIG. 5C). The effect was modest when compared to inhibition by synthetic peptides. Cell viability, determined by a tetrazolium based MTT assay, was not affected by the application of aminoglycosides at the mentioned concentrations (FIG. 5E).

In order to visualize the retrocyclins expressed by application of aminoglycosides, immunostaining was performed. TZM-bl cells were treated with PBS control or 10 μg/ml tobramycin and stained with anti-retrocyclin antibody or preimmune serum. Control cells showed no staining while cells treated with tobramycin revealed brightly stained cells suggesting that aminoglycosides can induce the expression of retrocyclin peptides (FIG. 5D).

TZM-bl cells were incubated with tobramycin (10 μg/ml) for 24 hr, and then treated the cells with preimmune or anti-retrocyclin serum followed by infection with HIV-1. FIG. 5F reveals that cells treated with preimmune serum showed a modest yet significant reduction in infection as compared to cells treated with anti-retrocyclin antibodies ($P<0.018$), suggesting that the antibody inhibited the endogenous retrocyclins. These data confirm that the anti-HIV-1 activity observed is due to the endogenous retrocyclin peptides expressed when tobramycin was applied to cells.

Figure 6:
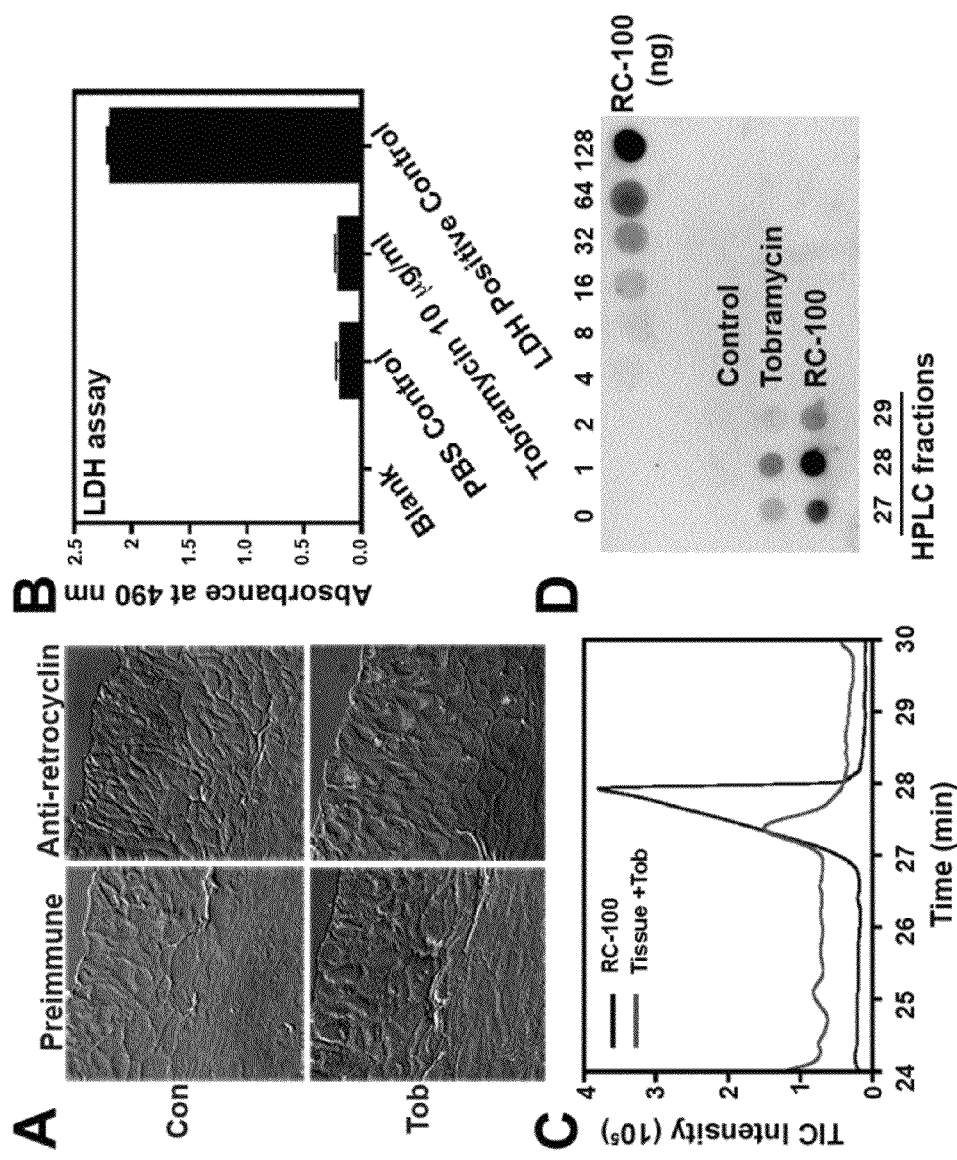
FIG. 6: Expression of retrocyclins in cervicovaginal tissue model using aminoglycosides. (A) Cervicovaginal tissues were treated with PBS (Con) or 10 μl tobramycin (Tob) and incubated with rabbit pre-immune serum or anti-retrocyclin antibody. The slides were then incubated with biotinylated goat anti-rabbit IgG secondary antibody and then stained using FITC-avidin. (B) Cytotoxicity was determined by measuring Lactate dehydrogenase (LDH) activity in media underlying the tissues treated with PBS or tobramycin as indicated. Bars represent absorbance measured as 490 nm and error bars represent SEM; n=6. (C) HPLC trace of extracts of tissues treated with 10 μg/ml tobramycin (Tissue+Tob) and 20 μg of synthetic RC-100. (D) RC-100 synthetic peptide (indicated amounts), HPLC fractions 27-29 of control, tobramycin-treated and RC-100 were dotted on a PVDF membrane and analyzed by immuno-dotblot.

Referring to FIGS. 6A-6D, the ability of aminoglycosides to induce the expression of retrocyclin peptides in an organotypic model cervicovaginal tissue was analyzed. Tissues were treated apically with tobramycin or control (PBS) for 24 hr and anti-retrocyclin immunohistochemical analysis was performed. Tissues treated with tobramycin alone and stained with anti-retrocyclin antibody revealed brightly stained cells (FIG. 6A) suggesting that production of retrocyclin peptides is induced upon application of aminoglycosides. Lactate Dehydrogenase (LDH) activity in the medium underlying the tissues was performed to determine tissue cytotoxicity. The LDH assay revealed that application of 10 μg/ml tobramycin was not cytotoxic to the tissues (FIG. 6B). In addition, treatment of tobramycin did not affect the metabolic activity adversely, which was determined by an MTT assay performed on one tissue (data not shown).

In order to purify endogenous retrocyclins expressed in the tissues, reverse-phase HPLC was utilized. FIG. 6C shows an HPLC trace of control, tobramycin-treated tissue extracts as compared to synthetic RC-100 peptide. Synthetic RC-100 peptide was recovered in fractions collected at 27-29 minutes. Corresponding fractions from control and tobramycin-treated tissues were analyzed by immuno-dotblot analysis using the anti-RC-101 antibody. FIG. 6D shows that retrocyclin polypeptides were recovered in the 27-29 min fractions in tobramycin-treated tissue samples, but not in control tissue samples. The amount of retrocyclin polypeptides (e.g., RC-100) expressed in tobramycin-treated cervicovaginal tissues was estimated by densitometry to be approximately 1.6 μg/tissue. Together these studies show that aminoglycosides suppress the premature termination codon of retrocyclin transcripts and restore the ability of cervicovaginal tissues to protect cells from HIV-1.

Accordingly, in another aspect of the present invention, there is provided a process for inducing the expression of a retrocyclin polypeptide in a mammalian host cell. The host cell has a naturally-occurring sequence encoding for the retrocyclin polypeptide, wherein the naturally-occurring sequence has a premature termination codon. The process comprises inducing expression of the retrocyclin polypeptide in the host cell via contacting the host cell with an amount of a read-through mediating agent effective to read-through the premature termination codon and allow for expression of the retrocyclin polypeptide. In one embodiment, the read-through mediating agent comprises an aminoglycoside. In a particular embodiment, the aminoglycoside is one or more of amikacin, arbekacin, gentamycin, kanamycin, neomycin, netilmicin, paromomycin, rhodostreptomycin, streptomycin, tobramycin, and apramycin. In one embodiment, the host cell is a mammalian host cell, e.g., a human host cell. The host cell may be a mucosal cell, an ocular cell, an epithelial cell, a cervicovaginal cell, or promyelocytic cells, for example.

In accordance with another aspect of the present invention, there is provided a process for inhibiting HIV-1 virus entry into a host cell of a mammalian subject comprising administering to the mammalian subject an amount of a read-through mediating agent effective to induce expression of a retrocyclin polypeptide in the host cell. In one embodiment, the read-through mediating agent is an aminoglycoside that is formulated into a topical composition and administered topically. In another embodiment, the aminoglycoside is administered orally in a suitable formulation, optionally comprising pharmaceutical carriers and excipients as are known in the art. In a particular embodiment, the host cell is a female human cell and the read-through mediating agent is administered topically to a vaginal mucosa of the subject. In yet another embodiment, the host cell is a nasal cell or nasal mucosal cell, and the read-through mediating agent is administered topically to the nasal mucosa of the subject.

In accordance with another aspect of the present invention, there is provided a pharmaceutical composition for inhibiting HIV-1 cell entry comprising an amount of an aminoglycoside effective to induce expression of a retrocyclin polypeptide in a mammalian host cell. In one embodiment, the pharmaceutical composition, or a product made therefrom, is formulated to be consumed orally. In another embodiment, the pharmaceutical composition, or a product made therefrom, is a pharmaceutical, an OTC medicament, an ointment, liquid, cream or other material suitable for topical application. Alternatively, the pharmaceutical composition may be formulated to be suitable for oral, rectal, optical, buccal (e.g., sublingual), parenteral (e.g., subcutaneous, intramuscular, intradermal and intravenous) and transdermal administration. In one exemplary embodiment, a product for topical application may comprise at least 0.01%, and up to 5.0%, by weight of the aminoglycoside. Different aminoglycosides are readily commercially available from suitable sources.

In addition, a topical composition may include other cosmetic and pharmaceutical actives and excipients as desired. Such suitable cosmetic and pharmaceutical agents include, but are not limited to, antifungals, vitamins, anti-inflammatory agents, antimicrobials, analgesics, nitric oxide synthase inhibitors, insect repellents, self-tanning agents, surfactants, moisturizers, stabilizers, preservatives, antiseptics, thickeners, lubricants, humectants, chelating agents, skin penetration enhancers, emollients, fragrances and colorants.

Further, any embodiment of the pharmaceutical composition may include one or more pharmaceutically acceptable adjuvants, carriers and/or excipients. Pharmaceutically acceptable adjuvants, carriers and/or excipients are well known in the art, for example as described in the Handbook of Pharmaceutical Excipients, second edition, American Pharmaceutical Association, 1994 (the entirety of which is incorporated by reference herein).

A pharmaceutical composition suitable for oral administration may be prepared in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions can be prepared by any suitable method of pharmacy, which includes the step of bringing into association the read-through mediating agent, e.g., an aminoglycoside, and one or more suitable carriers (which can contain one or more accessory ingredients as noted above). Generally, the compositions of the invention are prepared by uniformly and intimately admixing the aminoglycoside with a liquid or finely divided solid carrier, or both, and then, if necessary, shaping the resulting mixture. For example, a tablet can be prepared by comprising or molding a powder or granules containing the extract, optionally with one or more accessory ingredients. Compressed tablets can be prepared by compressing in a suitable machine, the extracts in the form of a powder or granules optionally mixed with a binder, lubricant, inert diluents, and/or surface active/dispersing agent(s). Molded tablets can be made by molding, in a suitable machine, the powdered compound moistened with an inert liquid binder.

Suitable fillers for orally administrable pharmaceutical compositions, such as sugars, e.g., lactose, saccharose, mannitol or sorbitol, cellulose preparations and/or calcium phosphates, e.g., tricalcium phosphate or calcium hydrogen phosphate, and also binders such as starch paste using, e.g., corn, wheat, rice or potato starch, gelatin, tragacanth, methylcellulose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients can be flow conditioners and lubricants, for example silicic acid, talc, stearic acid or salts thereof, such as magnesium or calcium stearate, and/or polyethylene glycol. Tablets, capsules, or Dragee cores can be provided with suitable, optionally enteric, coatings, there being used, inter alia, concentrated sugar solutions which can comprise gum arabic, talc, polyvinylpyrrolidone, polyethylene glycol and/or titanium dioxide, or coating solutionsin suitable organic solvents or solvent mixtures, or, for the preparation of enteric coatings, solutions of suitable cellulose preparations, such as acetylcellulose phthalate or hydroxypropylmethylcellulose phthalate. Dyes or pigments can be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticizer, such as glycerol or sorbitol. The dry-filled capsules can comprise the extracts in the form of granules, for example in admixture with fillers, such as lactose, binders, such as starches, and/or glicants, such as talc or magnesium stearate, and, where appropriate, stabilizers. In soft capsules, the extract is preferably dissolved or suspended in suitable liquids, such as fatty oils, paraffin oil or liquid polyethylene glycols, to which stabilizers can also be added.

In summary, identifying effective drugs to prevent sexually transmitted infections and other viral or bacterial infections is essential for countering the spread of these diseases. Exogenous (synthetic) retrocyclin polypeptides exhibit full activity in the complex environment of vaginal fluid and the peptide is very well tolerated in organotypic human cervicovaginal tissue models [17]. Moreover, HIV-1 evolves little resistance during continued passaging in the presence of the peptide [18]. For these and other reasons, retrocyclins have emerged as potential topical microbicides to protect against sexually-transmitted HIV-1 infections.

In the present invention, the present inventor has developed novel and nonobvious human pseudogenes that encode the demidefensin precursors whose post-translational processing gives rise to mature retrocyclin peptides are expressed at the mRNA level in multiple organs, including the spleen, bone marrow, thymus, testis and skeletal muscle [14] and cervicovaginal epithelia. By transfecting host cells, e.g., human myeloid cells, ocular cells, or mucosal cells, with delivery vectors, e.g., plasmids, comprising containing retrocyclin constructs without a premature termination codon, it was demonstrated that the "machinery" needed to process, trim, splice and oxidize retrocyclin precursors was available in human cells, e.g., human myeloid or mucosal cells. Two sets of expression constructs were transfected into cells: a shorter form (R1R3) that terminates at the end of the retrocyclin gene and a longer form that contains (A1A3) additional 3' untranslated residues (UTR). A1A3 cells expressed higher levels of retrocyclin peptides as compared to R1R3 cells indicating a role for additional residues in the translational efficiency of these peptides. While not wishing to be bound by theory, it is believed this may due to the fact that the length of the 3'-UTR regulates translation efficiency [28, 30]. Further, the present inventor has found that aminoglycoside-treated cells and cervicovaginal tissues may express retrocyclin polypeptides by suppressing the premature termination codon in their endogenous mRNA transcript.

In one embodiment, the methods, constructs, and pharmaceutical products described herein are effective for preventing and/or treating sexually transmitted infections (STI's) including, but not limited to, HIV-1, HIV-2, and other bacterial infections. For example, in one embodiment, the methods, constructs, and pharmaceutical products described herein may be useful in preventing nasal carriage of *Staphylococcus aureus*.

Since approximately 30% of inherited disorders may result from premature termination codon mutations, there has been tremendous interest and some progress in developing and applying agents that can read-through premature UAA, UAG or UGA termination codons [25]. In a sense, human retrocyclin-deficiency is also an inherited disorder, albeit one with an incidence of 100%. It is caused by a premature termination codon mutation that occurred after human lineage diverged from the lineage we share with orangutans, lesser apes and old world monkeys. Since HIV-1 and other viruses that currently infect humans have evolved in the absence of selective pressure exerted by retrocyclins, the ability to reawaken this ancestral molecule could be used to strengthen the innate immune system's ability to prevent or limit the infections they now induce.

Example 1

Maintenance of Cells, Tissues and Viruses

HL60 cells [33, 34] obtained from ATCC were cultured in Iscoves's DMEM with 20% FBS, 100 U/ml penicillin and 100 µg/ml streptomycin (I20). TZM-bl cells [35] stably expressing CD4, CCR5 & CXCR4, has firefly luciferase gene under the control of HIV-1 promoter (from Dr. Kappes, Dr. Wu and Tranzyme Inc). TZM-bl, HOS-CD4-CCR5 [36, 37] (from Dr. Landau), PM1 cells [38], (from Dr. Reitz) and HIV-1 BaL, an R5 tropic strain, were all procured through the NIH AIDS Research and Reference Reagent program. HIV-1 BaL viral stocks were prepared by infecting PM1 cells [18]. Peripheral blood mononuclear cells (PBMC) were isolated from blood drawn from a healthy HIV-1 seronegative donor as per the guidelines of the institutional review board of University of Central Florida. PBMCs were isolated using Lymphosep® (MP biomedicals LLC, Solon, Ohio), and cultured in RPMI-1640 medium with 10% FBS (R10) supplemented with 50 Units of IL-2 (R10-50U) and 5 µg/ml of phytohemagglutinin (PHA) for 3 days. The cells were then resuspended in R10-50U at a density of 0.8×10⁶ cells/ml and grown for 5-6 days.

Cervicovaginal tissues (EpiVaginal™) were obtained from MatTek Corp., Ashland, Mass. and maintained in proprietary growth medium as per the company's guidelines. The tissues were composed of a full-thickness, stratified vaginal-ectocervical layer intermixed with Langehans cells and underlying lamina propria. The tissues were allowed to grow on transwell cell culture inserts at the air-liquid interface.

Example 2

Creation of Retrocyclin Constructs and Stably Transfected HL60 Cells

Retrocyclin cDNA was amplified from human bone marrow cDNA and cloned into pCRII-TOPO vector (Invitrogen, Carlsbad, Calif.). Cole et al, *Proc Natl Acad Sci USA*. 2002 Feb. 19; 99(4): 1813-1818, provides information on the human retrocyclin gene and protein, which reveals the termination codon (x) 17 at the 17 codon position (see FIG. 1). Two mutations, Termination codon ((x)17)→Gln (Q17) and Arg (R70)→Lys (K70) were introduced, either (x)17Q alone (RC-100) or both (RC-101) using Quick Change® site-directed mutagenesis (Stratagene, LaJolla, Calif.) and subcloned in-frame into the phCMV-luc-FSR vector (Genlantis, San Diego, Calif.) to generate four constructs R1, R3, A1 and A3 (FIG. 1A). Plasmids R1 and A1 encode RC-100 nonapeptide while R3 and A3 encode RC-101 nonapeptide. Constructs A1 and A3 have a longer insert that includes additional downstream residues. HL60 cells (10⁷ cells/400 µl Iscove's DMEM) were co-transfected with 2 µg each of linearized R1, R3 or A1, A3 or phCMV-luc vector alone, by electroporation (exponential decay wave mode—280 V; 975 µF) and selected in I20 medium with 300 µg/ml G418 sulfate. Stable transfectants thus produced were named according to the constructs used for co-transfection (R1R3, A1A3 or Vector Control: VC). Presence of these constructs in the cells was verified using PCR of genomic DNA (FIG. 7A). PCR conditions used were the following: initial denaturation at 95° C. for 3 min; 30 cycles of 95° C. for 1 min, 58° C. for 1 min, 72° C. for 2 min followed by a final extension at 72° C. for 7 min. Sequences of the primers used for the PCR reaction are listed in Table 1. RNA was extracted from 10⁶ cells (HL60, VC, R1R3 and A1A3) using TRIzol (Invitrogen), cleaned with DNaseI (Ambion Inc., Austin Tex.) and cDNA synthesized (iScript™, BioRad, Hercules Calif.). Expression of recombinant genes was verified by PCR from the cDNA and subsequent restriction digestion using HpyCH4V (New England Biolabs, Beverly, Mass.) (FIGS. 7B and 7C).

Example 3

Acid Extraction and Affinity Purification of Retrocyclin Peptides

HL60 cells (control, VC, R1R3 and A1A3) were extracted with 5% acetic acid by vortexing for 20 min, centrifuged for 10 min at 10,000×g, supernatants were then vacuum-dried and resuspended in 0.01% acetic acid. HL60 acid extracts (equivalent of 20×10⁶ cells) were affinity purified using anti-RC-101 polyclonal antisera immobilized to a Carbolink™ coupling gel (Pierce Biotechnology Inc. Rockford, Ill.) prepared according to the manufacturer's instructions. Immunopurified samples were desalted using Sep-Pak C-18 cartridges (Waters Corp., Milford, Mass.). The elutes were then dried and resuspended in 100 µl of 0.01% acetic acid. 100 µg of synthetic RC-101 peptide was also affinity purified as positive control (RC-101 IP).

Example 4

Luciferase-Based Infection Assay to Determine Anti-HIV-1 Activity

TZM-bl cells (4000 cells/well; 96-well plate) were infected with HIV-1 Ba L (2-6.5 ng/ml of p24$^{gag}$) in the presence of vehicle (0.01% acetic acid) or HL60 extracts (from 0.25×10⁶ control or A1A3 or R1R3 cells) or affinity purified extracts (from 0.625×10⁶ control HL60 or VC or R1R3 or A1A3 cells or RC-101 IP diluted 1:32 times) or RC-101 (20 µg/ml) (positive control) for 24 hr. Treatments were then removed and the infection was quantified by measuring luciferase using Bright-Glo reagents (Promega, Madison, Wis.) in an LMax luminometer (Molecular Devices, Sunnyvale, Calif.). Cytotoxicity and metabolic activity of cells were verified by a tetrazolium-based MTT assay (R&D systems, Minneapolis, Minn.) performed on identically treated cells.

Example 5

Antiviral Infection Assay in Suspension Cells and HIV-1 p24$^{gag}$ ELISA

Acid extracts of stably transfected HL60 cells were vacuum-dried and resuspended in PBS. PM1 cells (10⁵ cells) or PBMCs (10⁶ cells) were treated with PBS (vehicle) or HL60 extracts (from 10⁴ cells for PM1 and 10⁵ for PBMCs) of control cells or A1A3 cells or 10 µg/ml of synthetic RC-101 and infected with HIV-1 BaL (2 ng of p24/ml) in 100 µl of RPMI medium with 20% FBS (R20) for 2 hr. Cells were then washed with 2 ml of R20, resuspended in fresh medium containing the treatments and cultured for 5-9 days. Subsequently, on alternate days culture supernatants were collected and fresh medium with the corresponding treatments was added. Viability of the cells was measured using trypan blue exclusion assay. Amount of HIV-1 virus in the culture supernatants was quantified by ELISA for HIV-1 p24$^{gag}$ (Perkin Elmer, Waltham, Mass.).

Peptides RC-100, RC-100b, RC-101, RC-101_2K, synthetic protegrin-1 (PG-1), Rhesus theta defensin-1 (RTD-1) and human neutrophil peptides 1-3 (HNP 1-3) or unknown samples were dotted (4 µl dot) as indicated on a 0.22 µm PVDF membrane (Immobilon-P) that was activated with methanol and presoaked in TBS. The membrane was then probed with 1:1000 rabbit anti-RC-101 antibody and developed using Immun™-star HRP reagent (BioRad) [17].

Example 6

Immunostaining of Stably Transfected HL60 Cells Using Anti-RC-101 Antibody

HL60 cells (VC, R1R3 and A1A3) were fixed on slides (100,000 cells/slide), immersed in 10% Formalin in PBS for 10 min, washed (PBS for 2 min), incubated in Target retrieval solution (Dako North America Inc., Carpinteria, Calif.) for 20 min at 95° C., cooled to 25° C., washed, blocked (2% Goat Serum, 0.1% Triton-X, 0.05% Tween-20, antibody buffer (10 mg/ml BSA/1 mg/ml gelatin/PBS) for 20 min and incubated in rabbit pre-immune serum or rabbit anti-RC-101 antibody (1:5000 in antibody buffer) overnight. Slides were washed, incubated in biotinylated goat anti-rabbit IgG antibody (1:20,000 in 1% goat serum/PBS for 30 min), followed by additional washing and treatment with Fluorescein-Avidin D (Vector Laboratories Inc.; 1:500 in PBS for 30 min). Cover slips were mounted using Vectashield fluorescence mounting medium and visualized using a Zeiss Axiovert 200M microscope system.

Tissues for immunofluorescence staining were fixed in 4% paraformaldehyde and slides were prepared by Mass Histology (Worcester, Mass.). The slides were deparaffinized, washed with TBS, and stained with anti-retrocyclin or preimmune serum and immunostained the same way as cells. The slides were then visualized on a Zeiss Axiovert 200M microscope system with 450 ms exposure time for all slides.

Example 6

Separation of Proteins from Stably Transfected HL60 Extracts Using Reverse-Phase HPLC Acid extracts from control HL60 and A1A3 cells (equivalent of $100 \times 10^6$ cells) were separated by RP-HPLC using the Alliance HT Waters 2795 Separations Module on a $C_{18}$ Column equilibrated in solvent A (aqueous 0.1% TFA). Elution was done with a gradient of 0-95% solvent B (0.08% TFA in acetonitrile), for 75 min, at 1 ml/min. Collected fractions (1 ml each) were vacuum dried and reconstituted in 100 μl of 0.01% acetic acid. Synthetic RC-101 peptide (control) was recovered from the fractions eluting at 26-28 min. A1A3 HPLC fractions (#23-28) were electrophoresed on a 16% Tricine-SDS gel and electroblotted on a 0.22 μm PVDF membrane at 180 mA for 22 min. The western blot membrane was then processed as described [17] and developed with Chemi-Glow reagent (Alpha Innotech, San Leandro, Calif.). A1A3 RP-HPLC fractions (27-30 min) were pooled and the concentration was determined to be (2.13 ng/μl) by densitometry measurements using Quantity one 1-D analysis (BioRad). A luciferase-based assay was used to verify the activity of A1A3 HPLC fractions (diluted 3 times in D10) against HIV-1 BaL (2 ng p24/ml).

MatTek cervicovaginal tissues treated with PBS (control) or 10 μg/ml tobramycin were extracted with T-PER® reagent (Pierce Biotechnology Inc. Rockford, Ill.) and separated by RP-HPLC. 20 μg of synthetic retrocyclin (RC-100) was also separated as a positive control. Synthetic RC-100 was eluted in fractions collected at 27-29 min. Tissue samples eluted at 27-29 min were vacuum-dried to near dryness and resuspended in 100 μl of 0.01% acetic acid. HPLC fractions (27-29 min) of MatTek tissue extracts (control or tobramycin-treated) and synthetic RC-100 were analysed by immunodotblot analysis.

Example 7

Mass Spectrometric Analysis

A1A3 HPLC Fraction 26, RC-101 and RC-101_2K were reduced, alkylated and treated with Lys-C protease for 30 min before analyzing by mass spectrometry. In brief, 20 mM Tris [2-carboxyethyl]phosphine (TCEP) was used to reduce (30 min at 25° C.) the samples, alkylated by incubating the samples with iodoacetamide (60 mM; 45 min at 25° C.; pH 8-9) followed by digestion with Lys-C (Wako Chemicals, Richmond, Va.; 30 min at 37° C.) and subjected to MALDI-TOF-MS analysis using a model 4700 Proteomics Analyzer (Applied Biosystems, Foster City, Calif.) as described previously [39]. Lys-C digested RC-101 was desalted using C18 ZipTip (Millipore Corp., Billerica, Mass.) and subjected to Edman degradation on cLC-Procise sequencer (Applied Biosystems, Forest City, Calif.).

Example 8

Aminoglycoside Mediated Read-Through of Termination Codon

Wildtype and mutant retrocyclin cDNAs were subcloned into phCMV-luc-FSR vector to create unrescued RC-101 and rescued RC-101 C-terminal luciferase fusion constructs, and verified by sequencing. HOS-CD4-CCR5 cells were cultured in antibiotic free growth medium (D10⁻) and co-transfected with 0.5 μg of unrescued or rescued (positive control) RC-101 plasmids along with 0.1 μg of phRL-CMV vector (transfection control containing renilla luciferase gene) using Effectene transfection reagent (Qiagen, Valencia, Calif.). The next day cells were treated for 24 hr with the appropriate aminoglycoside (40 μg/ml amikacin or 5 μg/ml gentamicin or 10 μg/ml tobramycin) or D10⁻ for control cells. Read-through was determined by measuring luciferase and renilla levels using a dual luciferase assay (Promega Corp., Madison, Wis.).

TZM-bl cells (4000 cells/well; 96 well plate) were cultured in D10⁻ and treated with vehicle (PBS buffered D10⁻) or peptides RC-101 or RC-100 (2.5 μg/ml each) as positive control or aminoglycosides as before for 30 min followed by infection with HIV-1 BaL (p24 of 2 ng/ml) at 37° C. for 24 hr. Subsequently, viral infection was quantified by measuring luciferase levels using Bright-Glo reagents (Promega). Cellular metabolism was monitored by measuring reduction in the ability of cellular dehydrogenases to reduce MTT to formazan (R&D Systems).

TZM-bl cells were cultured on coverslips and treated with PBS control or 10 μg/ml of tobramycin for 24 hr. The coverslips were then processed for immunofluorescence staining with anti-retrocyclin (rabbit anti-RC-101 antibody) or preimmune serum as described above.

For antibody-mediated neutralization experiments, TZM-bl cells (4000 cells/well; 96 well plate) were cultured in D10⁻ medium and treated with vehicle (PBS) or 10 μg/ml of tobramycin for 24 hr. The next day, cells were treated with either rabbit preimmune or anti-retrocyclin serum diluted 1:10 in D10⁻ medium containing tobramycin or RC-100 (2.5 μg/ml). Two hours later the cells were infected with HIV-1 BaL (p24 of 5 ng/ml) at 37° C. for 24 hr. Viral infection was quantified as described above. An MTT assay was performed to confirm that the treatments were not cytotoxic (data not shown).

Example 9

Application of Aminoglycosides to Organotypic Cervicovaginal Tissue Model

Cervicovaginal tissues were treated topically with 100 μl of PBS (control; n=4) or with 10 μg/ml of tobramycin (n=8) for 24 hr. Viability was assessed on control and tobramycin-treated tissue (n=1) using MTT assay kit (MatTek Corp., Ashland, Mass.). Cytotoxicity was measured by quantifying lactate dehydrogenase (LDH) activity in the underlying medium collected 24 hr after treatment with PBS or tobramycin by using CytoTox96 non-radioactive cytotoxicity assay kit (Promega Corp., Madison, Wis.).

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims. The teachings of all cited references are incorporated herein in their entirety to the extent not inconsistent with the teachings herein.

REFERENCES

1. Zarocostas J (2007) WHO and UN slash their estimates of global HIV prevalence. BMJ 335: 1069.
2. Bokazhanova A, Rutherford G W (2006) The epidemiology of HIV and AIDS in the world. Coll Antropol 30 Suppl 2: 3-10.
3. Titti F, Cafaro A, Ferrantelli F, Tripiciano A, Moretti S, et al. (2007) Problems and emerging approaches in HIV/AIDS vaccine development. Expert Opin Emerg Drugs 12: 23-48.
4. Cole A M, Hong T, Boo L M, Nguyen T, Zhao C, et al. (2002) Retrocyclin: a primate peptide that protects cells from infection by T- and M-tropic strains of HIV-1. Proc Natl Acad Sci USA 99: 1813-1818.
5. Munk C, Wei G, Yang O O, Waring A J, Wang W, et al. (2003) The theta-defensin, retrocyclin, inhibits HIV-1 entry. AIDS Res Hum Retroviruses 19: 875-881.
6. Cole A M, Wang W, Waring A J, Lehrer R I (2004) Retrocyclins: using past as prologue. Curr Protein Pept Sci 5: 373-381.
7. Wang W, Owen S M, Rudolph D L, Cole A M, Hong T, et al. (2004) Activity of alpha- and theta-defensins against primary isolates of HIV-1. J Immunol 173: 515-520.
8. Owen S M, Rudolph D L, Wang W, Cole A M, Waring A J, et al. (2004) RC-101, a retrocyclin-1 analogue with enhanced activity against primary HIV type 1 isolates. AIDS Res Hum Retroviruses 20: 1157-1165.
9. Ganz T (1999) Defensins and host defense. Science 286: 420-421.
10. Cole A M (2003) Minidefensins and other antimicrobial peptides:candidate anti-HIV microbicides. Expert Opin Ther Targets 7: 329-341.
11. Tang Y Q, Yuan J, Osapay G, Osapay K, Tran D, et al. (1999) A Cyclic Antimicrobial Peptide Produced in Primate Leukocytes by the Ligation of Two Truncated à-Defensins. Science 286: 498-502.
12. Trabi M, Schirra H J, Craik D J (2001) Three-dimensional structure of RTD-1, a cyclic antimicrobial defensin from Rhesus macaque leukocytes. Biochemistry 40: 4211-4221.
13. Tran D, Tran P A, Tang Y Q, Yuan J, Cole T, et al. (2002) Homodimeric theta-defensins from Rhesus macaque leukocytes-Isolation, synthesis, antimicrobial activities, and bacterial binding properties of the cyclic peptides. Journal of Biological Chemistry 277: 3079-3084.
14. Nguyen T X, Cole A M, Lehrer R I (2003) Evolution of primate theta-defensins: a serpentine path to a sweet tooth. Peptides 24: 1647-1654.
15. Gallo S A, Wang W, Rawat S S, Jung G, Waring A J, et al. (2006) Theta-defensins prevent HIV-1 Env-mediated fusion by binding gp41 and blocking 6-helix bundle formation. Journal of Biological Chemistry 281: 18787-18792.
16. Fuhrman C A, Warren A D, Waring A J, Dutz S M, Sharma S, et al. (2007) Retrocyclin RC-101 overcomes cationic mutations on the heptad repeat 2 region of HIV-1 gp41. FEBS J 274: 6477-6487.
17. Cole A L, Herasimtschuk A, Gupta P, Waring A J, Lehrer R I, et al. (2007) The retrocyclin analogue RC-101 prevents human immunodeficiency virus type 1 infection of a model human cervicovaginal tissue construct. Immunology 121: 140-145.
18. Cole A L, Yang O O, Warren A D, Waring A J, Lehrer R I, et al. (2006) HIV-1 adapts to a retrocyclin with cationic amino acid substitutions that reduce fusion efficiency of gp41. J Immunol 176: 6900-6905.
19. Keeling K M, Bedwell D M (2002) Clinically relevant aminoglycosides can suppress disease-associated premature stop mutations in the IDUA and P53 cDNAs in a mammalian translation system. J Mol Med 80: 367-376.
20. Wilschanski M, Yahav Y, Yaacov Y, Blau H, Bentur L, et al. (2003) Gentamicin-induced correction of CFTR function in patients with cystic fibrosis and CFTR stop mutations. N Engl J Med 349: 1433-1441.
21. Lai C H, Chun H H, Nahas S A, Mitui M, Gamo K M, et al. (2004) Correction of ATM gene function by aminoglycoside-induced read-through of premature termination codons. Proc Natl Acad Sci USA 101: 15676-15681.
22. Brooks D A, Muller V J, Hopwood J J (2006) Stop-codon read-through for patients affected by a lysosomal storage disorder. Trends Mol Med 12: 367-373.
23. Nudelman I, Rebibo-Sabbah A, Shallom-Shezifi D, Hainrichson M, Stahl I, et al. (2006) Redesign of aminoglycosides for treatment of human genetic diseases caused by premature stop mutations. Bioorg Med ChemLett 16: 6310-6315.
24. Sermet-Gaudelus I, Renouil M, Fajac A, Bidou L, Parbaille B, et al. (2007) In vitro prediction of stop-codon suppression by intravenous gentamicin in patients with cystic fibrosis: a pilot study. BMC Med 5: 5.
25. Zingman L V, Park S, Olson T M, Alekseev A E, Terzic A (2007) Aminoglycoside-induced translational read-through in disease: overcoming nonsense mutations by pharmacogenetic therapy. Clin Pharmacol Ther 81: 99-103.
26. Lynch S R, Puglisi J D (2001) Structural origins of aminoglycoside specificity for prokaryotic ribosomes. J Mol Biol 306: 1037-1058.
27. Lynch S R, Puglisi J D (2001) Structure of a eukaryotic decoding region A-site RNA. J Mol Biol 306: 1023-1035.
28. Tanguay R L, Gallie D R (1996) Translational efficiency is regulated by the length of the 3' untranslated region. Mol Cell Biol 16: 146-156.
29. Daly N L, Chen Y K, Rosengren K J, Marx U C, Phillips M L, et al. (2007) Retrocyclin-2: structural analysis of a potent anti-HIV theta-defensin. Biochemistry 46: 9920-9928.
30. Mazumder B, Seshadri V, Fox P L (2003) Translational control by the 3'-UTR: the ends specify the means. Trends Biochem Sci 28: 91-98.
31. Du M, Liu X, Welch E M, Hirawat S, Peltz S W, et al. (2008) PTC124 is an orally bioavailable compound that promotes suppression of the human CFTR-G542X nonsense allele in a CF mouse model. Proc Natl Acad Sci USA 105: 2064-2069.
32. Welch E M, Barton E R, Zhuo J, Tomizawa Y, Friesen W J, et al. (2007) PTC124 targets genetic disorders caused by nonsense mutations. Nature 447: 87-91.
33. Gallagher R, Collins S, Trujillo J, McCredie K, Ahearn M, et al. (1979) Characterization of the continuous, differen- 34. Collins S J, Gallo R C, Gallagher R E (1977) Continuous growth and differentiation of human myeloid leukaemic cells in suspension culture. Nature 270: 347-349.
35. Platt E J, Wehrly K, Kuhmann S E, Chesebro B, Kabat D (1998) Effects of CCR5 and CD4 cell surface concentrations on infections by macrophagetropic isolates of human immunodeficiency virus type 1. J Virol 72: 2855-2864.
36. Deng H, Liu R, Ellmeier W, Choe S, Unutmaz D, et al. (1996) Identification of a major co-receptor for primary isolates of HIV-1. Nature 381: 661-666.
37. Landau N R, Littman D R (1992) Packaging system for rapid production of murine leukemia virus vectors with variable tropism. J Virol 66: 5110-5113.
38. Lusso P, Cocchi F, Balotta C, Markham P D, Louie A, et al. (1995) Growth of macrophage-tropic and primary human immunodeficiency virus type 1 (HIV-1) isolates in a unique CD4+ T-cell clone (PM1): failure to downregulate CD4 and to interfere with cell-line-tropic HIV-1. J Virol 69: 3712-3720.
39. Venkataraman N, Cole A L, Svoboda P, Pohl J, Cole A M (2005) Cationic polypeptides are required for anti-HIV-1 activity of human vaginal fluid. J Immunol 175: 7560-7567.

SEQUENCE LISTING

```
SEQ. ID. NO: 8:Arg Cys Ile Cys Gly Arg Gly Ile Cys
SEQ. ID. NO: 9:Arg Cys Ile Cys Gly Lys Gly Ile Cys
SEQ. ID. NO: 1:CGT TGT ATT TGT GGT CGT GGT ATT TGT
SEQ. ID. NO: 2:CGC TGC ATC TGC GGC CGC GGC ATC TGC
SEQ. ID. NO: 3:CGT TGT ATT TGT GGT AAA GGT ATT TGT
SEQ. ID. NO: 4:CGC TGC ATC TGC GGC AAG GGC ATC TGC
SEQ. ID. NO: 5  DNA
       1      ggagacccgg gacagaggac tgctgtctgc cctccctctt cactctgcct accttgagga
      61      tctgtcaccc cagccatgag gaccttcgcc ctcctcactg ccatgcttct cctggtggcc
     121      ctgtaggctc aggcggagcc acttcaggca agagctgatg aagctgcagc ccaggagcag
     181      cctggagcag atgatcagga aatggctcat gcctttacat ggcatgaaag tgccgctctt
     241      ccgctttcag actcagcgag aggcttgagg tgcatttgcg gaagaggaat ttgccgtttg
     301      ttataacgtc gctttgggtc ctgcgccttt cgtggtacac tccaccggat ctgctgccgc
     361      tgagcttgca gaatcaagaa acataagctc agaatttact ttgagagtta aagaaattc
     421      ttgttactcc tgtaccttgt cctccatttc cttttctcat ccaaaataaa taccttgttg
     481      caagatttct ctcttt
```

TABLE 1

Primers used for verification of retrocyclin constructs.

| Primer Name | Sequence | Accession Number | Primer Location | Template |
|---|---|---|---|---|
| DEFT_Fwd | TCCTCACTGC CATGCTTCT | AF526271.1 | 29-47 | Genomic DNA |
|  |  | AF355799 | 92-110 | cDNA |
| DEFT_Rev | TTATAACAAAC GGCAAATTCCT | AF526271.1 | 897-918 | Genomic DNA |
|  |  | AF355799 | 285-306 | cDNA |

The invention claimed is:

1. A method for inducing the expression of a retrocyclin polypeptide to reduce infection in a mammalian vaginal mucosal cell having a naturally-occurring sequence encoding for the retrocyclin polypeptide, the naturally-occurring sequence having a premature termination codon, the method comprising:

inducing expression of the retrocyclin polypeptide in the mammalian vaginal mucosal cell to reduce infectious agent entry into the mucosal cell by contacting the vaginal mucosal cell with an amount of a read-through mediating agent effective to read-through the premature termination codon and allow for expression of the retrocyclin polypeptide;

wherein the read-through mediating agent comprises at least one of gentamicin and tobramycin.

2. A method for reducing infectious agent entry into a vaginal mucosa of a mammalian subject having a naturally-occurring sequence encoding for a retrocyclin polypeptide, the naturally-occurring sequence having a premature termination codon, the method comprising:

administering to the vaginal mucosa of the mammalian subject an amount of a read-through mediating agent effective to read-through the premature termination codon to induce expression of the retrocyclin polypeptide that reduces infectious agent entry into the vaginal mucosa, wherein the read-through mediating agent comprises at least one of gentamicin and tobramycin.

* * * * *

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Retrocyclin

<400> SEQUENCE: 1
cgttgtattt gtggtcgtgg tatttgt              27

<210> SEQ ID NO 2
<211> LENGTH: 27
<212> TYPE: DNA
<213> ORGANISM: Artificial Sequence
<220> FEATURE:
<223> OTHER INFORMATION: Retrocylin -continued

```
<400> SEQUENCE: 2
cgctgcatct gcggccgcgg catctgc                                           27

<210> SEQ ID NO 3
<211> LENGTH: 27
<212> TYPE: DNA
<213> ORGANISM: Artificial Sequence
<220> FEATURE:
<223> OTHER INFORMATION: Retrocylin

<400> SEQUENCE: 3
cgttgtattt gtggtaaagg tatttgt                                           27

<210> SEQ ID NO 4
<211> LENGTH: 27
<212> TYPE: DNA
<213> ORGANISM: Artificial Sequence
<220> FEATURE:
<223> OTHER INFORMATION: Retrocylins

<400> SEQUENCE: 4
cgctgcatct gcggcaaggg catctgc                                           27

<210> SEQ ID NO 5
<211> LENGTH: 496
<212> TYPE: DNA
<213> ORGANISM: Artificial Sequence
<220> FEATURE:
<223> OTHER INFORMATION: Retrocylin

<400> SEQUENCE: 5
ggagacccgg gacagaggac tgctgtctgc cctccctctt cactctgcct accttgagga       60
tctgtcaccc cagccatgag gaccttcgcc ctcctcactg ccatgcttct cctggtggcc      120
ctgtaggctc aggcggagcc acttcaggca agagctgatg aagctgcagc ccaggagcag      180
cctggagcag atgatcagga aatggctcat gcctttacat ggcatgaaag tgccgctctt      240 ccgcttcag actcagcgag aggcttgagg tgcatttgcg gaagaggaat ttgccgtttg       300
ttataacgtc gctttgggtc ctgcgccttt cgtggtacac tccaccggat ctgctgccgc      360
tgagcttgca gaatcaagaa acataagctc agaatttact ttgagagtta aagaaattc       420 ttgttactcc tgtaccttgt cctccatttc cttttctcat ccaaaataaa taccttgttg      480
caagatttct ctcttt                                                      496

<210> SEQ ID NO 6
<211> LENGTH: 19
<212> TYPE: DNA
<213> ORGANISM: Homo sapiens

<400> SEQUENCE: 6
tcctcactgc catgcttct                                                    19

<210> SEQ ID NO 7
<211> LENGTH: 22
<212> TYPE: DNA
<213> ORGANISM: Homo sapiens

<400> SEQUENCE: 7
ttataacaaa cggcaaattc ct                                                22

<210> SEQ ID NO 8
<211> LENGTH: 27
```

```
<212> TYPE: PRT
<213> ORGANISM: Artificial Sequence
<220> FEATURE:
<223> OTHER INFORMATION: Retrocylin

<400> SEQUENCE: 8

Ala Arg Gly Cys Tyr Ser Ile Leu Glu Cys Tyr Ser Gly Leu Tyr Ala
1               5                   10                  15

Arg Gly Gly Leu Tyr Ile Leu Glu Cys Tyr Ser
            20                  25

<210> SEQ ID NO 9
<211> LENGTH: 27
<212> TYPE: PRT
<213> ORGANISM: Artificial Sequence
<220> FEATURE:
<223> OTHER INFORMATION: Retrocylin

<400> SEQUENCE: 9

Ala Arg Gly Cys Tyr Ser Ile Leu Glu Cys Tyr Ser Gly Leu Tyr Leu
1               5                   10                  15

Tyr Ser Gly Leu Tyr Ile Leu Glu Cys Tyr Ser
            20                  25

<210> SEQ ID NO 10
<211> LENGTH: 9
<212> TYPE: PRT
<213> ORGANISM: Homo sapiens

<400> SEQUENCE: 10

Arg Cys Ile Cys Gly Arg Gly Ile Cys
1               5
```